United States Patent [19]

Trybulski

[11] 4,379,090
[45] Apr. 5, 1983

[54] PROCESS FOR THE PREPARATION OF 1-(PHENYL AND HALOPHENYL)-3,4-DIHYDRO-4-[(DIMETHYLAMINO)METHYLENE]5H-2-BENZAZEPIN-5-ONE-2-OXIDES

[75] Inventor: Eugene J. Trybulski, Parsippany, N.J.

[73] Assignee: Hoffmann-La Roche Inc., Nutley, N.J.

[21] Appl. No.: 324,293

[22] Filed: Nov. 23, 1981

Related U.S. Application Data

[60] Division of Ser. No. 150,509, May 16, 1980, Pat. No. 4,318,854, which is a continuation-in-part of Ser. No. 10,118, Feb. 7, 1979, abandoned.

[51] Int. Cl.³ .......................................... C07D 223/16
[52] U.S. Cl. ............................................. 260/239 BB
[58] Field of Search ................................. 260/239 BB

[56] References Cited

PUBLICATIONS

Elderfield, "Heterocyclic Compounds", vol. 9, pp. 334, 335, Wiley & Sons, New York, N.Y., (1967).

Primary Examiner—Nicholas S. Rizzo
Assistant Examiner—D. B. Springer
Attorney, Agent, or Firm—Jon S. Saxe; Bernard S. Leon; Frank P. Hoffman

[57] ABSTRACT

Compounds of the formula

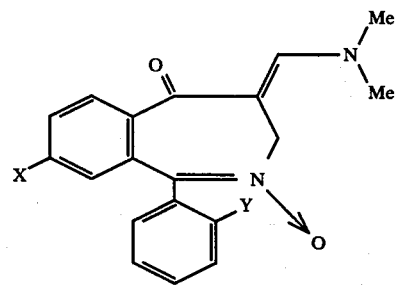

wherein X and Y are selected from the group consisting of hydrogen, halogen and trifluoromethyl, are disclosed.

The compounds are useful as intermediates in the production of 2-benzazepines, compounds of pharmacological activity.

Also disclosed are other intermediates and processes for their production.

1 Claim, No Drawings

PROCESS FOR THE PREPARATION OF 1-(PHENYL AND HALOPHENYL)-3,4-DIHYDRO-4-[(DIMETHYLAMINO)METHYLENE]5H-2-BENZAZEPIN-5-ONE-2-OXIDES

RELATED APPLICATIONS

This is a division of application Ser. No. 150,509, filed May 16, 1980, now U.S. Pat. No. 4,318,854, which is a continuation-in-part application of copending U.S. patent application Ser. No. 10,118, filed Feb. 7, 1979 now abandoned.

DESCRIPTION OF THE INVENTION

The present invention relates to compounds of the formula

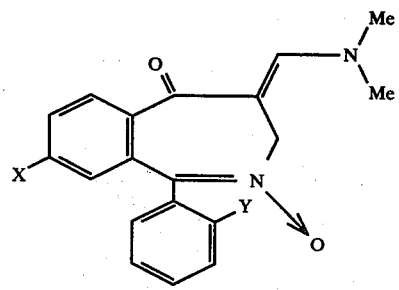

wherein X and Y are selected from the group consisting of hydrogen, halogen and trifluoromethyl.

The compounds are useful as intermediates in the production of 2-benzazepines, compounds useful as sedatives and anxiolytic agents.

As used in the present invention the term "halogen" or "halo" means all three forms thereof, i.e., chloro, bromo or fluoro.

The compounds of the present invention can be prepared by following the reaction schemes below:

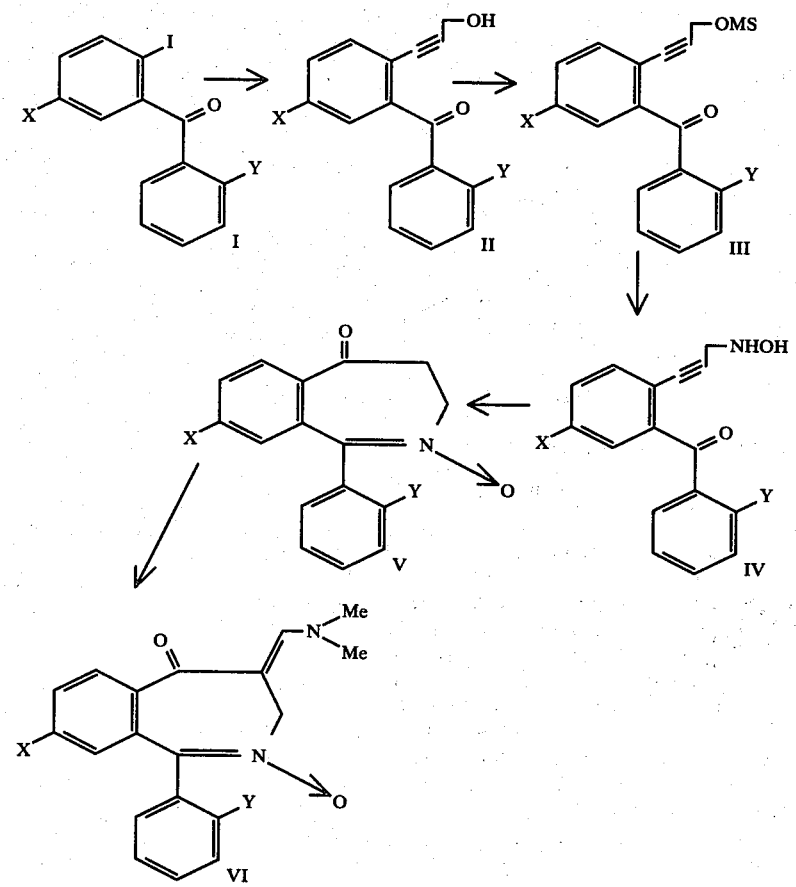

Scheme 1

Scheme 2

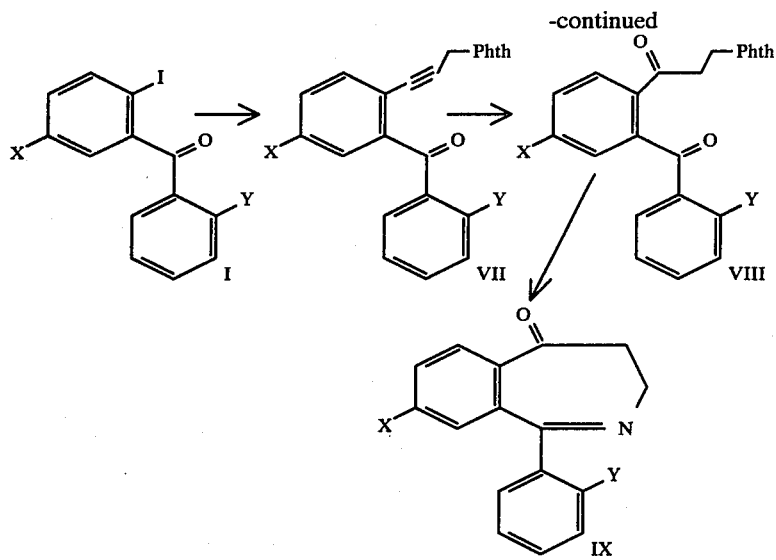

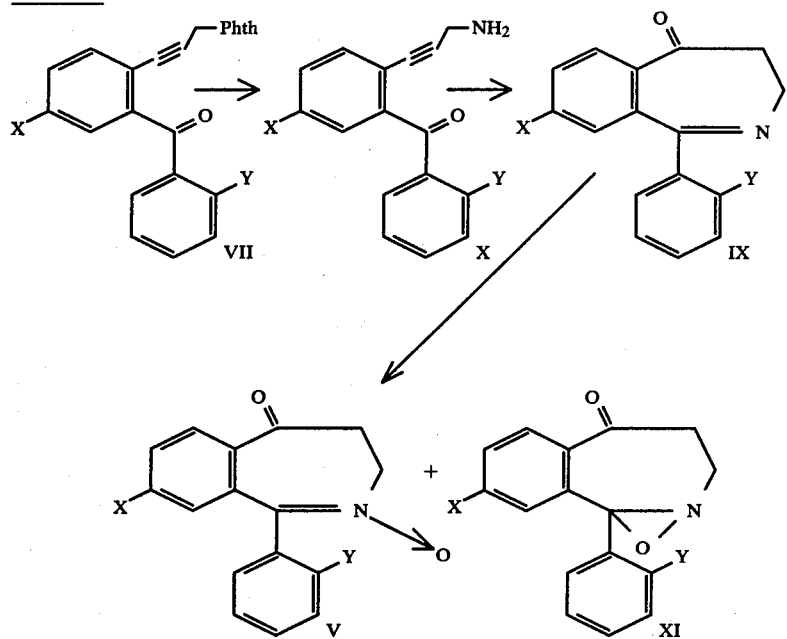

wherein X and Y are as above.

Scheme 1

I→II

The compund of formula II is produced by reacting the compound of formula I with propargyl alcohol in the presence of palladium chloride or acetate, cuprous iodide, an organophosphine, for example, triphenylphosphine, and a tertiary or secondary amine, such as, diethylamine or diisopropylamine. The reaction solvent may be the amine itself, e.g., diethylamine, a halogenated hydrocarbon, e.g., methylene chloride, dimethylformamide or ether solvents. The reaction temperature may range from about 0° C. to about 70° C. with ambient temperatures as preferred.

The presence of cuprous iodide is mandatory if the reaction is carried out at room temperature or below while this is not the case if the reaction is carried out with heating. The presence of the organophosphine is not absolutely necessary but highly advantageous. Instead of the palladium salt plus the organophosphine an appropriate complex such as dichloro bis(triphenylphosphine)palladium II can also be utilized.

The starting material of formula I may be produced by diazotizing the corresponding known aminobenzophenone using sodium nitrite in sulfuric acid and isolating the salts by precipitating the respective tetrafluoroborate salts which were thereafter slurried in water and treated with aqueous potassium iodide to give the iodobenzophenone. These reactions are carried out utilizing methods known in the art.

II→III

The compound of formula II is thereafter reacted with methanesulfonyl chloride and a tertiary amine, such as, triethylamine, in the presence of an organic solvent, such as, a halogenated hydrocarbon, e.g., methylene chloride or toluene or diethyl ether. The reaction can be run between about −78° C. and room temperature with about 0° C. as preferred. Compounds corresponding to those of formula III but which contain a suitable leaving group other than mesyloxy can also be prepared starting from compounds of formula II by methods known in the art, e.g., by means of toluenesulfonyl chloride, thionyl chloride, phosphorus tribromide and the like.

III→IV→V

The compound of formula III or an analog having a suitable leaving group is reacted with hydroxylamine in a $C_1$ to $C_4$ alcohol solvent at a reaction temperature of from about 0° C. to room temperature, with about room temperature as preferred. The isolated intermediate compound IV is thereafter reacted with a mixture of mercuric sulfate, chloride, acetate, or trifluoroacetate and a $C_1$ to $C_5$ carboxylic acid, e.g., formic or acetic acid in an inert solvent, such as, a halogenated hydrocarbon, e.g., methylene chloride. The reaction temperature ranges from about $-10°$ C. to room temperature with about 0° C. to 5° C. as preferred. Alternatively the compound of formula IV can be treated with a strong acid in the presence of water, e.g., sulfuric acid, at from about $-10°$ C. to room temperature with about 0° C. as preferred.

V→VI

The compound of formula V is reacted with dimethylformamide dimethylacetal in an inert solvent, such as, a halogenated hydrocarbon, e.g., methylene chloride or dimethylformamide or high boiling ethers. The reaction temperature may range from about 0° C. to 100° C. with room temperature as preferred.

Scheme 2

I→VII

The compound of formula I is reacted with propargyl phthalimide in the presence of palladium chloride, cuprous iodide, an organophosphine, e.g., triphenylphosphine and a secondary amine, such as, diethylamine or diisopropylamine. The solvents and reaction conditions are as previously disclosed for step I→II. Compounds corresponding to those of formula VII but which contain a suitable protected amino group other than phthalimido can also be prepared in a similar manner starting from compounds of formula IV by means of e.g. N-carbobenzoxy propargylamine or corresponding N-formyl, N-tert. butoxycarbonyl, N-acetyl or N-trifluoroacetyl compounds.

VII→VIII

The compound of formula VII or an analog having a suitable protected amino group is thereafter reacted with a mixture of mercuric sulfate and a $C_1$ to $C_4$ carboxylic acid, e.g., formic or acetic acid, in the presence of a halogenated hydrocarbon solvent, e.g., methylene chloride or an inert ether. The reaction temperature may range from about 0° C. to room temperature with about 0° C. as preferred. Alternatively the compound of formula VII or analog thereof can be treated with concentrated sulfuric acid at from about $-10°$ C. to room temperature with about 0° C. as preferred.

VIII→IX

The compound of formula VIII or an analog having a suitable protected amino group is thereafter reacted with a primary alkyl amine, e.g., methyl or ethylamine in a $C_1$ to $C_4$ alcohol solvent. The reaction temperature may range from about 0° C. to room temperature with room temperature as preferred.

Scheme 3

VII→X

The compound of formula VII is reacted with a primary alkyl amine, e.g., methyl or ethylamine or hydrazine in a water miscible solvent, such as, $C_1$ to $C_4$ alcohols or ethers or dimethylformamide. The reaction temperature may range from about 0° C. to 60° C. with about room temperature as preferred.

A second method which may be utilized to produce the compound of formula X consists of an acid or base hydrolysis of the compound of formula VII. For an acid hydrolysis, a 30% solution of a mineral acid, such as, hydrochloric, hydrobromic, sulfuric or phosphoric acid may be utilized. The reaction is run at or about reflux temperature. For a base hydrolysis, an alkali metal hydroxide, such as, potassium or sodium hydroxide is utilized. Inert organic solvents, such as those set forth above may be utilized to solubilize the ingredients. The reaction is run at or above reflux temperature of the selected solvent.

X→IX

The compound of formula X may thereafter be reacted with a mixture of mercuric sulfate and a $C_1$ to $C_4$ carboxylic acid as disclosed in step VII→VIII or may be reacted with concentrated sulfuric acid at from about $-10°$ C. to room temperature with about 0° C. as preferred.

IX→V→and XI

The compound of formula IX is reacted with a peracid, such as, metachloroperbenzoic acid in an inert organic solvent such as a halogenated hydrocarbon, e.g., methylene chloride or an ether. The reaction may be carried out from about 0° C. to 40° C. with about room temperature as preferred. The mixture of products may thereafter be separated from one another by fractional crystallization. Analysis by thin-layer chromatography indicates the presence of both products.

In the above scheme it should be noted that where the term "lower alkyl" or "alkyl" is utilized, there is meant a $C_1$ to $C_7$ ($C_1$ to $C_4$ preferred) straight or branched aliphatic hydrocarbon chain.

The compound of formula IX is a known intermediate in the art and is useful in the production of various benzazepines which are compounds of pharmacological utility, i.e., as anxiolytics, see, for example, U.S. Pat. Nos. 4,028,381; 4,022,800; 4,022,801 and 3,989,689. The present processes to produce IX offer an advantage over the prior art in that it involves fewer steps, is cheaper and affords better yields.

The intermediate compound of formula VI is also a useful intermediate for the production of 2-benzazepines, e.g., a pyrimido-2-benzazepines of the formula

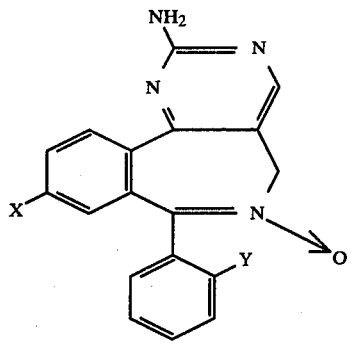

wherein X and Y are as above.

The above compounds are produced by the reaction of the compound of formula VI with a compound of the formula

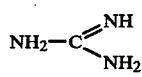

Any inert organic solvent such as methylene chloride, alcohols such as methanol, ethers such as dioxane, tetrahydrofuran or dimethylformamide may be utilized with a reaction temperature ranging from about room temperature to reflux temperature of the chosen solvent with about room temperature as preferred.

The above reaction does not form a part of the present invention, but is presented for completeness of disclosure relating to the utility of the instantly claimed compounds. These 2-benzazepines exhibit anxiolytic and sedative activities.

EXAMPLE 1

5-Chloro-2-iodobenzophenone

A mixture of 76 g (1.1 mole) of sodium nitrite and 450 ml of sulfuric acid was heated on a steam bath to ca 80° C. until complete solution was achieved. The solution was cooled to 30° C. and 232 g (1.0 mole) of 2-amino-5-chlorobenzophenone was added in portions keeping the temperature between 30° C. and 40° C. The mixture was stirred for 1 hr and then slowly poured into 3 l. of an ice and water mixture. The solution was filtered through Hy-Flo and to the stirred filtrate was added slowly a solution of 200 g (1.83 mole) of sodium fluoborate in 800 ml of water. The resulting precipitate was collected by filtration and washed with water (2×100 ml) to give a moist white solid.

The moist 2-benzoyl-4-chlorobenzenediazonium fluoborate was slurried in 3 l. of water, and a solution of 332 g (2 moles) of potassium iodide in 1 l. of water was added dropwise. The mixture was stirred at room temperature for 4 hr and the resulting precipitate was collected by filtration. The crude product was added to 1 l. of boiling ether, filtered, and dried with anhydrous sodium sulfate. The ether solution was concentrated to 500 ml and the addition of 100 ml of petroleum ether gave the product. A small amount of the material was recrystallized from a mixture of ether and petroleum ether to give fine yellow prisms, mp 80°–82° C.

EXAMPLE 2

5-Chloro-2'-fluoro-2-iodobenzophenone

The preparation of 5-chloro-2'-fluoro-2-iodobenzophenone was conducted in the same manner as the preparation of 5-chloro-2-iodobenzophenone to give light yellow prisms, mp 78°–81° C.

EXAMPLE 3

2',5-Dichloro-2-iodobenzophenone

Method A

The preparation of 2',5-dichloro-2-iodobenzophenone was conducted in the same manner as the preparation of 5-chloro-2-iodobenzophenone to give light yellow prisms, mp 64°–66° C.

Method B

A solution of 9.0 g (0.13 mole) of sodium nitrite in 30 ml of water was added dropwise to a solution of 27 g (0.1 mole) of 2-amino-2',5-dichlorobenzophenone in 50 ml of acetic acid and 30 ml of sulfuric acid which was cooled to 0° C. Stirring at 0° C. was continued for 1.5 hr followed by the dropwise addition of 33 g (0.2 mole) of potassium iodide in 40 ml of water. The mixture was stirred at 0° C. for 2 hr. The mixture was diluted with water, and extracted with ether. The ether solution was washed with 5% aqueous sodium thiosulfate, dried over anhydrous sodium sulfate and concentrated at reduced pressure to a brown oil. Crystallization from cold ether gave the product, mp 63°–65° C. which was identical in every respect to an authentic sample.

EXAMPLE 4

2'-Chloro-2-iodobenzophenone

The preparation of 2'-chloro-2-iodobenzophenone was conducted in the same manner as 5-chloro-2-iodobenzophenone to give pale yellow prisms, mp 62°–64° C.

EXAMPLE 5

2-Iodobenzophenone

The preparation of 2-iodobenzophenone was conducted in the same manner as the preparation of 5-chloro-2-iodobenzophenone to give a brown oil. A small amount was purified by column chromatography to give white prisms, mp 29°–31° C.

EXAMPLE 6

1-[4-Chloro-2-benzoylphenyl]-3-phthalimidopropyne

A mixture of 0.71 g (4.0 mmole) of palladium chloride, 2.1 g (8.0 mmole) of triphenylphosphine, 0.80 g (4.2 mmole) of cuprous iodide, 68.8 g (0.21 mole) of 5-chloro-2-iodobenzophenone, 200 ml of diethylamine, and 400 ml of methylene chloride was stirred at room temperature under argon until complete solution was obtained. In one portion, 40.0 g (0.22 mole) of N-propargyl-phthalimide was added to the solution and the resulting mixture stirred for 20 hr. The volatiles were removed at reduced pressure and the residue was triturated with 200 ml of isopropanol. The resulting precipitate was collected by filtration to give the crude product mp 130°–133° C. Recrystallization from acetone gave cream colored prisms, mp 148°–150° C.

EXAMPLE 7

1-[4-Chloro-2-(2-fluorobenzoyl)phenyl]-3-phthalimidopropyne

The preparation of 1-[4-chloro-2-(2-fluorobenzoyl)-phenyl]-3-phthalimidopyropyne was conducted in the same manner as the preparation of 1-[4-chloro-2-benzoylphenyl]-3-phthalimidopropyne to give cream colored prisms, mp 158°–161° C.

EXAMPLE 8

1-[4-Chloro-2-(2-chlorobenzoyl)phenyl]-3-phthalimidopropyne

The preparation of 1-[4-chloro-2-(2-chlorobenzoyl)-phenyl]-3-phthalimidopropyne was conducted in the same manner as the preparation of 1-[4-chloro-2-benzoylphenyl]-3-phthalimidopropyne to give cream colored prisms, mp 144°–145° C.

EXAMPLE 9

1-[2-(2-Chlorobenzoyl)phenyl]-3-phthalimidopropyne

The preparation of 1-[2-(2-chlorobenzoyl)phenyl]-3-phthalimidopropyne was conducted in the same manner as the preparation of 1-[4-chloro-2-benzoylphenyl]-3-phthalimidopropyne to give cream colored prisms, mp 149°–150° C.

EXAMPLE 10

1-[2-Benzoylphenyl]-3-phthalimidopropyne

The preparation of 1-[2-benzoylphenyl]-3-phthalimidopropyne was conducted in the same manner as the preparation of 1-[4-chloro-2-benzoylphenyl]-3-phthalimidopropyne to give cream colored prisms, mp 164°–165° C.

EXAMPLE 11

3-Hydroxy-1-[4-chloro-2-benzoylphenyl]propyne

A mixture of 0.17 g (1.0 mmole) of palladium chloride, 0.5 g (2.0 mmole) of triphenylphosphine, 0.1 g (0.5 mmole) of cuprous iodide, 15 g (43 mmole) of 5-chloro-2-iodobenzophenone and 60 ml of diethylamine was stirred at room temperature for 20 min. In one portion 6.0 g (107 mmole) of propargyl alcohol was added, and the resulting mixture was stirred for 24 hr. The solvent was removed at reduced pressure and the residue was dissolved in ether. The ether solution was washed with water, dried with anhydrous sodium sulfate, and concentrated at reduced pressure to give the product as a red oil.

EXAMPLE 12

3-Hydroxy-1-[4-chloro-2-(2-fluorobenzoyl)phenyl]propyne

A mixture of 0.37 g (0.5 mmole) of dichlorobis (triphenylphosphine) palladium II, 70 mg (0.35 mmole) of cuprous iodide, 36.1 g (0.1 mole) of 5-chloro-2'-fluoro-2-iodobenzophenone and 12 ml (0.2 mole) of propargyl alcohol in 200 ml of diethylamine was stirred at room temperature for 4 days. The mixture was concentrated at reduced pressure and the residue was partitioned between ether and water. The ether layer was washed with water, dried over anhydrous sodium sulfate and concentrated at reduced pressure to give the product as an amber oil.

EXAMPLE 13

3-Hydroxy-1-[4-chloro-2-(2-fluorobenzoyl)phenyl]-propyne methanesulfonate

Dropwise 13 ml (0.17 mole) of methanesulfonyl chloride was added to a solution of 28.9 g (0.1 mole) of 3-hydroxy-1-[4-chloro-2-(2-fluorobenzoyl)phenyl]-propyne and 24.4 ml (0.175 mole) of triethylamine in 300 ml of methylene chloride which was cooled to 0° C. The mixture was washed with ice water, cold 1 N hydrochloric acid, cold saturated aqueous sodium bicarbonate and dried over anhydrous sodium sulfate. Concentration of the methylene chloride solution gave a brown oil which was crystallized from ether to give a yellow solid. Recrystallization from a mixture of ether and petroleum ether gave off-white prisms, mp 95°–96° C.

EXAMPLE 14

1-[4-Chloro-2-benzoylphenyl]-3-phthalimidopropan-1-one

A mixture of 20 g (50 mmole) of 1-[4-chloro-2-benzoylphenyl]-3-phthalimidopropyne, 1.0 g (3 mmole) of mercuric sulfate and 55 ml of formic acid in 50 ml of methylene chloride was stirred at room temperature for 30 min. The mixture was poured over ice and extracted with ethyl acetate. The ethyl acetate solution was dried over anhydrous sodium sulfate and concentrated at reduced pressure to dryness. The residue was crystallized from a mixture of ethyl acetate and ether to give a colorless solid. Recrystallization from acetone gave colorless prisms, mp 163°–164° C.

EXAMPLE 15

3-Amino-1-[4-chloro-2-benzoylphenyl]propyne

Method A

A mixture of 72 g (0.18 mole) of 1-[4-chloro-2-benzoylphenyl]-3-phthalimidopropyne, 90 ml of 40% aqueous methylamine, and 300 ml of ethanol was stirred at room temperature for 90 min. The mixture was diluted with 300 ml of ether, and the precipitate was removed by filtration. The filtrate was further diluted with 300 ml of ether, washed with water and dried over anhydrous sodium sulfate. Concentration of the ether solution at reduced pressure gave a brown oil, which when triturated with ether gave a yellow solid. Recrystallization from ether gave pale yellow prisms, mp 68°–69° C.

Method B

A mixture of 4 g (10 mmole) of 1-[4-chloro-2-benzoylphenyl]-3-phthalimidopropyne and 0.6 g (16 mmole) of 85% hydrazine hydrate in 150 ml of 95% ethanol was refluxed for 5.5 hr. The mixture was cooled and the insoluble precipitate removed by filtration. The filtrate was diluted with water, acidified with hydrochloric acid and extracted with ether. The aqueous solution was basified with dilute sodium carbonate and extracted with methylene chloride. The methylene chloride solution was dried over anhydrous sodium sulfate and concentrated at reduced pressure to dryness. The residue was crystallized from a mixture of ether and petroleum ether to give a pale yellow solid, mp 68°–69° C. which was identical in every respect to an authentic sample.

The hydrochloride salt of 3-amino-1-[4-chloro-2-benzoylphenyl]propyne was prepared by the addition of an excess of 6% methanolic hydrogen chloride to a methanol solution of the product and isolated by precipitating the salt with the addition of ether. Recrystallization from a mixture of methanol and ether gave the hydrochloride as white needles, mp 173°–174° C.

EXAMPLE 16

3-Amino-1-[4-chloro-2-(2-fluorobenzoyl)phenyl]-propyne

Method A

The preparation of 3-amino-1-[4-chloro-2-(2-fluorobenzoyl)phenyl]propyne was conducted in the same manner (Method A) as the preparation of 3-amino-1-[4-chloro-2-benzoylphenyl]propyne to give yellow prisms, mp 89°–91° C.

Method B

A mixture of 50 g of 1-[4-chloro-2-(2-fluorobenzoyl)phenyl]-3-phthalimidopropyne, 50 ml of 40% aqueous methylamine and 150 ml of dimethylformamide was stirred at room temperature for 25 min. Dropwise 500 ml of water was added, and the resulting precipitate was collected by filtration. The precipitate was dissolved in methylene chloride, dried over anhydrous sodium sulfate, and concentrated at reduced pressure to give a pale yellow solid. Recrystallization from ether gave pale yellow prisms, mp 89°–91° C. which were identical in every respect to an authentic sample.

Method C

A mixture of 400 g (0.96 mole) of 1-[4-chloro-2-(2-fluorobenzoyl)phenyl]-3-phthalimidopropyne, 1.3 l of ethanol and 300 ml of 40% aqueous methylamine was stirred at room temperature for 2 hr. Dropwise 2.8 l of water was added, and the resulting precipitate was collected by filtration to give a pale yellow solid, mp 79°–80° C. Recrystallization from ether gave pale yellow prisms, mp 89°–91° C. which were identical in every respect to an authentic sample.

EXAMPLE 17

3-Amino-1-[4-chloro-2-(2-chlorobenzoyl)phenyl]-propyne

The preparation of 3-amino-1-[4-chloro-2-(2-chlorobenzoyl)phenyl]propyne was conducted in the same manner as the preparation of 3-amino-1-[4-chloro-2-benzoylphenyl]propyne [Method A] to give pale yellow prisms, mp 81°–82° C.

EXAMPLE 18

3-Amino-1-[2-(2-chlorobenzoyl)phenyl]propyne

The preparation of 3-amino-1-[2-(2-chlorobenzoyl)phenyl]propyne was conducted in the same manner as the preparation of 3-amino-1-[4-chloro-2-benzoylphenyl]propyne [Method A] to give an amber oil.

The hydrochloride salt of 3-amino-1-[2-(2-chlorobenzoyl)phenyl]propyne was prepared by the addition of an excess of 6% methanolic hydrogen chloride to a methanol solution of the product and isolated by precipitating the salt by the addition of ether. Recrystallization from a mixture of methanol and ether gave the salt as white needles, mp 160°–162° C.

EXAMPLE 19

3-Amino-1-[2-benzoylphenyl]propyne

The preparation of 3-amino-1-[2-benzoylphenyl]propyne was conducted in the same manner as the preparation of 3-amino-1-[4-chloro-2-benzoylphenyl]propyne [Method A] to give an amber oil.

The hydrochloride salt of 3-amino-1-[2-benzoylphenyl]propyne was prepared by the addition of an excess of 6% methanolic hydrogen chloride to a methanol solution of the product and was isolated by precipitating the salt with the addition of ether. Recrystallization from a mixture of methanol and ether gave the salt as white needles, mp 157°–158° C.

EXAMPLE 20

8-Chloro-1-(2-fluorophenyl)-3,4-dihydro-5H-2-benzazepin-5-one

Method A

A solution of 14.4 g (50 mmole) of 3-amino-1-[4-chloro-2-(2-fluorobenzoyl)phenyl]propyne in 50 ml of methylene chloride was added to a solution of 3.0 g (10 mmole) of mercuric sulfate in 50 ml of formic acid, which was cooled to 0° C. The mixture was stirred at 0° C. for 3 hr, poured over ice, basified with ammonium hydroxide and extracted with methylene chloride. The methylene chloride solution was dried over anhydrous sodium sulfate and concentrated at reduced pressure to give a brown oil. The oil was dissolved in 25 ml of isopropanol and 4.8 g (50 mmole) of methanesulfonic acid was added. The resulting precipitate was collected by filtration to give the methanesulfonate salt of the product as off-white crystals. Recrystallization from a mixture of methylene chloride and isopropanol gave the methanesulfonate salt of the product as pale yellow rods, mp 176°–177° C.

A sample of the methanesulfonate salt was partitioned between methylene chloride and aqueous saturated sodium bicarbonate. The methylene chloride solution was dried over anhydrous sodium sulfate, concentrated at reduced pressure and the residue was crystallized from ether. Recrystallization from ether gave off-white prisms, mp 109°–110° C.

Method B

A solution of 200 g (0.69 mole) of 3-amino-1-[4-chloro-2-(2-fluorobenzoyl)phenyl]propyne in 500 ml of methylene chloride was added dropwise to 400 ml of concentrated sulfuric acid, which was cooled to 5° C. The mixture was stirred at 5° C. for 3 hr, poured over ice, basified with ammonium hydroxide and extracted with methylene chloride. The methylene chloride solution was dried over anhydrous sodium sulfate and concentrated at reduced pressure to give a brown oil. The brown oil was dissolved in 350 ml of a 2 M methanol solution of methanesulfonic acid and the salt of the product was precipitated by the addition of ether to give the salt as off-white rods. Recrystallization from a mixture of methylene chloride and isopropanol gave the methanesulfonate salt as off-white rods, mp 176°–177° C. which were identical in every respect to an authentic sample.

EXAMPLE 21

8-Chloro-1-phenyl-3,4-dihydro-5H-2-benzazepin-5-one

The preparation of 8-chloro-1-phenyl-3,4-dihydro-5H-2-benzazepin-5-one was conducted in the same manner as the preparation of 8-chloro-1-(2-fluorophenyl)-3,4-dihydro-5H-benzazepin-5-one (Method A) to give the methanesulfonate salt as off-white prisms, mp 187°–190° C.

EXAMPLE 22

8-Chloro-1-(2-chlorophenyl)-3,4-dihydro-5H-2-benzazepin-5-one

The preparation of 8-chloro-1-(2-chlorophenyl)-3,4-dihydro-5H-2-benzazepin-5-one was conducted in the same manner as the preparation of 8-chloro-1-(2-fluorophenyl)-3,4-dihydro-5H-2-benzazepin-5-one (Method A) to give the methanesulfonate salt as colorless needles, mp 180°–181° C.

EXAMPLE 23

1-(2-Chlorophenyl)-3,4-dihydro-5H-2-benzazepin-5-one

The preparation of 1-(2-chlorophenyl)-3,4-dihydro-5H-2-benzazepin-5-one was conducted in the same manner as the preparation of 8-chloro-1-(2-fluorophenyl)-3,4-dihydro-5-H-2-benzazepin-5-one (Method A) to give a pale yellow solid, mp 135°–137° C.

EXAMPLE 24

1-Phenyl-3,4-dihydro-5H-2-benzazepin-5-one

The preparation of 1-phenyl-3,4-dihydro-5H-2-benzazepin-5-one was conducted in the same manner as the preparation of 8-chloro-1-(2-fluorophenyl)-3,4-dihydro-5H-2-benzazepin-5-one (Method A) to give the methanesulfonate salt as off-white prisms, mp 196°–198° C.

EXAMPLE 25

8-Chloro-1-(2-fluorophenyl)-3,4-dihydro-4-[(dimethylamino)methylene]-5H-2-benzazepin-5-one Method A A mixture of 7.2 g (25 mmole) of 8-chloro-1-(2-fluorophenyl)-3,4-dihydro-5H-2-benzazepin-5-one and 50 ml of dimethylformamide dimethyl acetal was refluxed for 1 hr. The mixture was concentrated at reduced pressure to give tan crystals. Recrystallization from ether gave yellow prisms, mp 228°–233° C.

Method B

A mixture of 10 g (35 mmole) of crude 8-chloro-3,4-dihydro-1-(2-fluorophenyl)-5H-2-benzazepin-5-one and 10 g (84 mmole) of dimethylformamide dimethyl acetal in 10 ml of dimethylformamide was stirred at room temperature for 12 hr. The resulting precipitate was collected by filtration, and washed successively with ethanol and ether to give tan crystals which were identical in every respect to an authentic sample.

Method C

A solution of 100 g (0.35 mole) of 3-amino-1-[4-chloro-2-(2-fluorobenzoyl)phenyl]propyne in 200 ml of methylene chloride was added dropwise to 210 ml of 95% sulfuric acid, which was cooled to 5° C. The mixture was stirred at 5° C. for 3.5 hr. The dark, syrupy mixture was poured over 2.5 l of crushed ice, basified with 525 ml of concentrated ammonium hydroxide and extracted with methylene chloride. The methylene chloride solution was washed with water, dried over anhydrous sodium sulfate and concentrated at reduced pressure to give a brown oil.

The oil was dissolved in 200 ml of dimethylformamide dimethyl acetal and heated on a steam bath for 15 min. The mixture was cooled and the resulting precipitate was collected by filtration and washed successively with ethanol and ether. The product was air dried to give light tan crystals which were identical in every respect to an authentic sample.

EXAMPLE 26

8-Chloro-1-phenyl-3,4-dihydro-4-[(dimethylamino)methylene]-5H-2-benzazepin-5-one The preparation of 8-chloro-1-phenyl-3,4-dihydro-4-[(dimethylamino)methylene]-5H-2-benzazepin-5-one was conducted in the same manner as the preparation of 8-chloro-1-(2-fluorophenyl)-3,4-dihydro-4-[(dimethylamino)methylene]-5H-2-benzazepin-5-one (Method A) to give yellow prisms, mp 180°–183° C.

EXAMPLE 27

8-Chloro-1-(2-chlorophenyl)-3,4-dihydro-4-[(dimethylamino)methylene]-5H-2-benzazepin-5-one A mixture of 18.6 g (61 mmole) of 8-chloro-1-(2-chlorophenyl)-3,4-dihydro-5H-2-benzazepin-5-one and 149 ml of dimethylformamide dimethyl acetal was gently heated (ca 50° C.) for 12 hr. The mixture was concentrated at reduced pressure to dryness. The residue was crystallized from a mixture of ether and methylene chloride to give a yellow solid, mp 170°–171° C. Recrystallization from ether gave yellow prisms, mp 170°–171° C.

EXAMPLE 28

1-(2-Chlorophenyl)-3,4-dihydro-4-[(dimethylamino)methylene]-5H-2-benzazepin-5-one A mixture of 3.4 g (12.5 mmole) of 1-(2-chlorophenyl)-3,4-dihydro-5H-2-benzazepin-5-one and 28 ml of dimethylformamide dimethyl acetal was refluxed for 2 hr. The mixture was concentrated at reduced pressure and the resulting solid was triturated with ether to give a tan solid, mp 155°–157° C. Recrystallization from a mixture of methylene chloride and ether gave yellow prisms, mp 158°–159° C.

EXAMPLE 29

3,4-Dihydro-4-[(dimethylamino)methylene]-5H-2-benzazepin-5-one

A mixture of 5.2 g (22 mmole) of 3,4-dihydro-1-phenyl-5H-2-benzazepin-5-one and 43 ml of dimethylformamide dimethyl acetal was refluxed for 4 hr. The mixture was concentrated at reduced pressure to dryness. The residue was crystallized with ether to give a yellow solid, mp 131°–133° C. Recrystallization from ether gave yellow prisms, mp 131°–132° C.

EXAMPLE 30

8-Chloro-1-(2-fluorophenyl)-3,4-dihydro-5H-2-benzazepin-5-one-2-oxide

Method A

A mixture of 6.4 g (22 mmole) of 8-chloro-1-(2-fluorophenyl)-3,4-dihydro-5H-2-benzazepin-5-one and 6.4 g (34 mmole) of m-chloroperbenzoic acid in 350 ml of methylene chloride was stirred at room temperature for 2 hr. The methylene chloride solution was washed with saturated aqueous sodium bicarbonate and water, dried over anhydrous sodium sulfate and concentrated at reduced pressure to give a yellow oil. The oil was crystallized from a mixture of ether and petroleum ether to give off-white prisms, mp 166°–168° C. Recrystallization from a mixture of ether and methylene chloride gave colorless prisms, mp 168°–170° C.

Method B

A mixture of 5.8 g (16 mmole) of 3-hydroxy-1-[4-chloro-2-(2-fluorobenzoyl)phenyl]propyne methanesulfonate and 50 ml of methanolic solution of hydroxylamine (from 6.1 g, 88 mmole of hydroxylamine hydrochloride) in 50 ml of tetrahydrofuran was stirred at room temperature for 13 hr. The mixture was concentrated at reduced pressure and the residue was partitioned between methylene chloride and water. The methylene chloride solution was dried over anhydrous sodium sulfate and concentrated at reduced pressure to give an amber oil containing 3-hydroxyamino-1-[4-chloro-2-(2-fluorobenzoyl)-phenyl]propyne.

A solution of 3.4 g of the amber oil in 70 ml of methylene chloride was added dropwise to a mixture of 0.7 g (2.3 mmole) of mercuric sulfate and 17 ml of formic acid which was cooled to 0° C. The resulting mixture was stirred at room temperature overnight, poured over ice and basified with ammonium hydroxide. The methylene chloride solution was washed with water, dried over anhydrous sodium sulfate and concentrated at reduced pressure to give a yellow oil. Purification by column chromatography (silica gel, 50 g; 3:1 methylene chloride and ether, eluent) gave tan crystals, mp 165°–167° C. Recrystallization from a mixture of ether and methylene chloride gave pale yellow prisms, mp 167°–170° C. which were identical in every respect to an authentic sample.

EXAMPLE 31

8-Chloro-1-(2-chlorophenyl)-3,4-dihydro-5H-2-benzazepin-5-one-2-oxide

The preparation of 8-chloro-1-(2-chlorophenyl)-3,4-dihydro-5H-2-benzazepin-5-one-2-oxide was conducted in the same manner as the preparation of 8-chloro-1-(2-fluorophenyl)-3,4-dihydro-5H-2-benzazepin-5-one-2-oxide (Method A) to give yellow prisms, mp 184°–187° C.

EXAMPLE 32

8-Chloro-1-(2-fluorophenyl)-3,4-dihydro-4-[(dimethylamino)methylene]-5H-2-benzazepin-5-one-2-oxide A mixture of 3.4 g (11 mmole) of 8-chloro-1-(2-fluorophenyl)-3,4-dihydro-5H-2-benzazepin-5-one-2-oxide and 26 ml of dimethylformamide dimethyl acetal was stirred at room temperature for 12 hr. The mixture was diluted with ether and the precipitate collected to give a yellow solid, mp 175°–178° C. Recrystallization from a mixture of ether and ethyl acetate gave yellow needles, mp 193°–194° C.

EXAMPLE 33

8-Chloro-1-(2-chlorophenyl)-3,4-dihydro-4-[(dimethylamino)methylene]-5H-2-benzazepin-5-one-2-oxide The preparation of 8-chloro-1-(2-chlorophenyl)-3,4-dihydro-4-[(dimethylamino)methylene]-5H-2-benzazepin-5-one-2-oxide was prepared in the same manner as the preparation of 8-chloro-1-(2-fluorophenyl)-3,4-dihydro-4-[(dimethylamino)methylene]-5H-2-benzazepin-5-one-2-oxide to give yellow prisms, mp 196°–198° C.

EXAMPLE 34

8-Chloro-1-phenyl-3,4-dihydro-5H-2-benzazepin-5-one

A mixture of 2.1 g (5 mmole) of 1-[4-chloro-2-benzoylphenyl]-3-phthalimidopropan-1-one and 10 ml of 40% aqueous methylamine in 25 ml of ethanol was stirred at room temperature for 45 min. The mixture was poured into water and extracted with ether. The ether layer was dried over anhydrous sodium sulfate and concentrated at reduced pressure to dryness. The residue (1.4 g) was purified by plug filtration (silica gel; eluent, methylene chloride). The resulting oil was treated with a 1 M solution of methanolic methanesulfonic acid to give the methanesulfonate salt of the product, mp 187°–190° C., which was identical in every respect to an authentic sample.

I claim:
1. A process to produce a compound of the formula

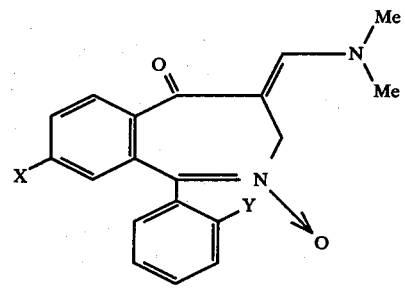

wherein X and Y are selected from the group consisting of hydrogen, halogen and trifluoromethyl, which consists essentially of:
(a) reacting a compound of the formula

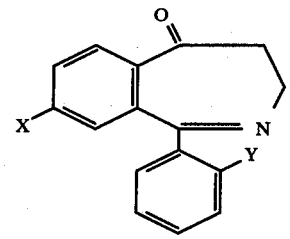

wherein X and Y are as above, with a peracid in an inert organic solvent at from about 0° C. to 40° C. and separating the analogous N-oxide thereof and
(b) thereafter reacting the N-oxide of step (a) with dimethylformamide dimethylacetal in an inert solvent at from about 0° C. to 100° C. to produce the end product.

* * * * *